(12) United States Patent
Chaiken et al.

(10) Patent No.: US 6,223,063 B1
(45) Date of Patent: Apr. 24, 2001

(54) METHOD AND DEVICE FOR TISSUE MODULATION

(75) Inventors: Joseph Chaiken, Fayetteville, NY (US); Charles M. Peterson, Potomac, MD (US)

(73) Assignee: LighTouch Medical, Inc., New Hope, PA (US)

( * ) Notice: Subject to any disclaimer, the term of this patent is extended or adjusted under 35 U.S.C. 154(b) by 0 days.

(21) Appl. No.: 09/238,487

(22) Filed: Jan. 27, 1999

Related U.S. Application Data

(60) Provisional application No. 60/072,658, filed on Jan. 27, 1998, and provisional application No. 60/072,710, filed on Jan. 27, 1998.

(51) Int. Cl.[7] .................................................. A61B 5/00
(52) U.S. Cl. ............................................ 600/310; 600/335
(58) Field of Search ................................... 600/310, 322, 600/323, 334, 335, 344

(56) References Cited

U.S. PATENT DOCUMENTS

| | | | |
|---|---|---|---|
| 5,099,842 | * | 3/1992 | Mannheimer et al. ............... 600/323 |
| 5,313,940 | * | 5/1994 | Fuse et al. ........................... 600/323 |
| 6,088,540 | * | 7/2000 | Leidig et al. ........................ 396/155 |

FOREIGN PATENT DOCUMENTS

| | | |
|---|---|---|
| 19 09 882 | 9/1970 | (DE) . |
| 0 573 137 | 12/1993 | (EP) . |
| WO93/00856 | 1/1993 | (WO) . |
| WO93/12712 | 7/1993 | (WO) . |
| WO94/10901 | 5/1994 | (WO) . |

* cited by examiner

Primary Examiner—Eric F. Winakur
(74) Attorney, Agent, or Firm—Gates & Cooper LLP

(57) ABSTRACT

Disclosed is a tissue modulation device comprising an upper surface and a lower surface, wherein the upper surface comprises a recessed region adjacent to a raised region, wherein the device is optically transparent in at least one of the recessed region or the raised region, wherein application of a first portion of a tissue to the raised region depresses the first portion of the tissue relative to a second portion of the tissue that is in apposition to the recessed region, and wherein the optically transparent region of the device is curved at the lower surface to substantially reduce backscattered light in a light path traveling through the optically transparent region to a light collection system. Also disclosed is a method of noninvasive spectroscopic measurement of an analyte in a subject. The method comprises applying tissue of the subject to a tissue modulation device comprising a recessed region adjacent to a raised region so that the raised region depresses a first portion of tissue relative to a second portion of tissue in apposition to the recessed region; irradiating the tissue in a blood-replete state with electromagnetic radiation having an excitation wavelength; collecting the spectra emitted by the tissue in the blood-replete state; irradiating the tissue in a blood-depleted state with electromagnetic radiation having an excitation wavelength; collecting the spectra emitted by the tissue in the blood-depleted state; and analyzing the collected spectra to determine a concentration of analyte present in the tissue, wherein the analyzing comprises determining the difference between the spectra collected in the blood-replete and blood-depleted states.

42 Claims, 7 Drawing Sheets

METHOD AND DEVICE FOR TISSUE MODULATION

This application claims the benefit of U.S. provisional patent applications Ser. Nos. 60/072,658 and 60/072,710, filed Jan. 27, 1998, the entire contents of which are hereby incorporated by reference into this application.

Throughout this application various publications are referenced. The disclosures of these publications in their entireties are hereby incorporated by reference into this application in order to more fully describe the state of the art to which this invention pertains.

TECHNICAL FIELD OF INVENTION

The invention relates to a method and device for modulating blood flow in tissue. Mechanical pressure is applied to a region of tissue in order to affect the flow and presence of blood in the associated capillary bed. The method facilitates the noninvasive measurement of blood analytes.

BACKGROUND OF THE INVENTION

There has long been considerable interest in the noninvasive monitoring of body chemistry. There are 16 million Americans with diabetes, all of whom would benefit from a method for noninvasive measurement of blood glucose levels. Using currently accepted methods for measuring blood glucose levels, many diabetics must give blood five to seven times per day to adequately monitor their health status. With a noninvasive blood glucose measurement, closer control could be imposed and the continuing damage, impairment and costs caused by diabetes could be minimized.

Blood oximetry is an example of an application of electronic absorption spectroscopy to noninvasive monitoring of the equilibrium between oxygenated and deoxygenated blood (U.S. Pat. No. 5,615,673, issued Apr. 1, 1997). Similarly, vibrational spectroscopy is a reliable mode of quantitative and qualitative ex vivo analysis for complex mixtures, and there are reports of in vitro applications of this method to metabolically interesting analytes (S. Y. Wang et al, 1993, Analysis of metabolites in aqueous solution by using laser Raman spectroscopy, Applied Optics 32(6):925–929; A. J. Berger et al., 1996, Rapid, noninvasive concentration measurements of aqueous biological analytes by near infrared Raman spectroscopy, Applied Optics 35(1):209–212). Infrared measures, such as vibrational absorption spectroscopy, have been applied to skin tissue, but with success limited by unavailability of suitable light sources and detectors at crucial wavelengths, and by heating of the tissue due to the absorption of incident radiation (U.S. Pat. No. 5,551,422, see also R. R. Anderson and J. A. Parrish, 1981, The Optics of Human Skin, J. Investigative Dermatology 77(1):13–19). Previous attempts to provide methods for noninvasive blood glucose monitoring are summarued in U.S. Pat. No. 5,553,616, issued on Sep. 10, 1996.

Optimal application of noninvasive techniques for blood analysis will require improved methods for isolating signals attributable to blood versus surrounding tissues.

SUMMARY OF THE INVENTION

The invention provides a device and methods to meet this need for obtaining signals related to blood analytes. The invention provides a tissue modulation device comprising an upper surface and a lower surface, wherein the upper surface comprises a recessed region adjacent to a raised region, wherein the device is optically transparent in at least one of the recessed region or the raised region, wherein application of a first portion of a tissue to the raised region depresses the first portion of the tissue relative to a second portion of the tissue that is in apposition to the recessed region, and wherein the optically transparent region of the device is curved at the lower surface to substantially reduce backscattered light in a light path traveling through the optically transparent region to a light collection system. In one embodiment, the raised region is opaque. In another embodiment, the raised region is optically transparent. In one embodiment, the recessed region is optically transparent. The recessed region can optionally be recessed relative to an adjacent portion of the upper surface of the device.

In one embodiment, the device further comprises a series of alternating recessed and raised regions coupled so as to form a continuous loop, and at least one rotatable sprocket engaged with the loop such that rotation of the sprocket effects rotation of the loop. The raised region can comprise a substantially cylindrical roller. The recessed region can comprise a length having a first end and a second end, and the recessed region can further comprise a substantially rectangular cross-section, adjoined at an end by a portion having a substantially circular cross-section.

The invention additionally provides a method of noninvasive spectroscopic measurement of an analyte in a subject. The method comprises applying tissue of the subject to a tissue modulation device comprising a recessed region adjacent to a raised region so that the raised region depresses a first portion of tissue relative to a second portion of tissue in apposition to the recessed region. The method further comprises irradiating the tissue in a blood-replete state with electromagnetic radiation having an excitation wavelength, and collecting the spectra emitted by the tissue in the blood-replete state. The method further comprises irradiating the tissue in a blood-depleted state with electromagnetic radiation having an excitation wavelength, and collecting the spectra emitted by the tissue in the blood-depleted state. The collected spectra are then analyzed to determine a concentration of analyte present in the tissue. The analyzing comprises determining the difference between the spectra collected in the blood-replete and blood-depleted states. The spectra are preferably Raman spectra. Examples of other spectra include, but are not limited to, NMR, ESR, UV visible absorption, IR absorption, fluorescence and phosphorescence spectra.

DETAILED DESCRIPTION

Figure 1:
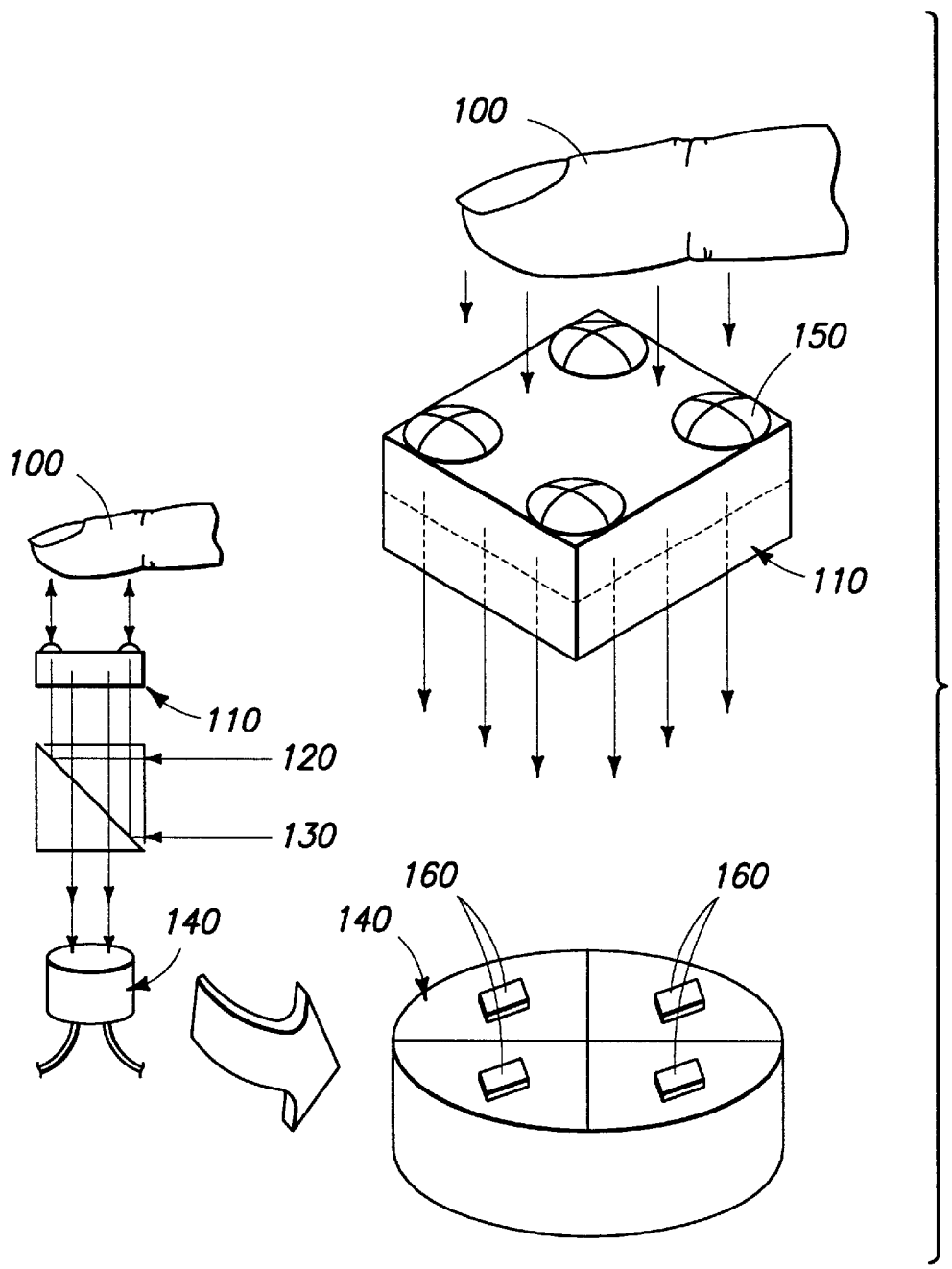
FIG. 1 is a representation of one embodiment of a static tissue modulation device 110 for use in conjunction with a quadrant detector 140.

Tissue modulation refers to manipulating the tissue to which the method is applied so that measurements, such as spectroscopic measurements, can be made in both blood replete and blood depleted states. One strategy for tissue modulation is the application of pressure to an area of tissue, such as a finger tip. When pressure is applied, the region of tissue is depleted of blood. When pressure is released or reduced, blood returns to the affected tissue. The difference between measurements taken in the blood replete and blood depleted states provides a measure indicative of components in the blood while mining the effects of extraneous spectroscopic signals due to calluses, dirt, soap residue and other sources associated with the surrounding tissue. When tissue modulation is employed during noninvasive spectroscopy, for example, the analysis can include determining the difference between the spectra collected in the blood replete and blood depleted states.

Definitions

All scientific and technical terms used in this application have meanings conmmonly used in the art unless otherwise specified. As used in this application, the following words or phrases have the meanings specified.

As used herein, "tissue" means any portion of an organ or system of the body, including, but not limited to, skin, capillary beds, blood, muscle, breast and brain.

As used herein, "Raman spectra associated with" a given component refers to those emitted Raman spectra which one skilled in the art would attribute to that component. One can determine which Raman spectra are attributable to a given component by irradiating that component in a relatively pure form, and collecting and analyzing the Raman spectra emitted by the component in the relative absence of other components.

As used herein, "blood replete" refers to a state in which blood flow through a tissue is unobstructed by, for example, vasoconstriction induced by cooling or the application of pressure. The blood replete state can be enhanced by conditions which increase vasodilation, such as warming.

As used herein, "blood depleted" refers to a state in which blood flow through a tissue is substantially restricted and blood volume is minimized. A blood depleted state can be achieved by, for example, cooling and/or applying pressure to the tissue.

As used herein, "opaque" refers to the optical property of an object such that light is substantially prevented from passing through the object. In preferred embodiments of the tissue modulation device, no light passes through the opaque regions.

As used herein, "optically transparent" refers to the optical property of an object such that light is permitted to pass through the object.

As used herein, "portion of tissue" refers to an area of tissue that light penetrates, and from which a signal is collected.

As used herein, "recessed region" refers to an area which is recessed relative to the raised area and may or may not be recessed relative to the immediately surrounding surface.

Methods of the Invention

The invention provides a method of measurement of blood volume simultaneously with measurements of a signal or signals indicative of one or more blood analytes. The blood volume measurement permits normalization of blood analyte measurements to allow computation of concentration levels. Temperature and pressure can be used to affect the capillary content and, although these can be controlled to a large extent, it is desirable to use tissue modulation apparatus to aid in the normalization. The invention provides a method for normalization that is less vulnerable to error due to differences between individual anatomy and blood flow patterns.

The invention provides a method of noninvasive spectroscopic measurement of an analyte in a subject. In one embodiment, the method comprises applying tissue of the subject to a tissue modulation device comprising a recessed region adjacent to a raised region so that the raised region depresses a first portion of tissue relative to a second portion of tissue in apposition to the recessed region. The method further comprises irradiating the tissue in a blood-replete state with electromagnetic radiation having an excitation wavelength and collecting the spectra emitted by the tissue in the blood-replete state. The method further comprises irradiating the tissue in a blood-depleted state with electromagnetic radiation having an excitation wavelength and collecting the spectra emitted by the tissue in the blood-depleted state. The method additionally comprises analyzing the collected spectra to determine a concentration of analyte present in the tissue, wherein the analyzing comprises determining the difference between the spectra collected in the blood-replete and blood-depleted states. Examples of spectra that can be collected include, but are not limited to, Raman, nuclear magnetic resonance (NMR), electron spin resonance (ESR), UV visible absorption, infrared absorption, fluorescence and phosphorescence spectra.

In one embodiment, the tissue is applied to the device with sufficient pressure to achieve the blood-depleted state in the first portion of the tissue that is in contact with the raised region. The pressure with which the tissue is applied can be such that the blood-replete state is simultaneously achieved in the second portion of the tissue that is in contact with the recessed region of the device. In another embodiment, the blood-replete state and the blood-depleted state are achieved at different points in time in the first portion of the tissue by varying the amount of pressure with which the tissue is applied to the raised region of the device. In another embodiment, the blood-replete state and the blood-depleted state are achieved in the first portion of the tissue by alternately applying the raised region and the recessed region to the first portion of the tissue.

Various modifications of the device can be made to accommodate different embodiments of the method. For example, the recessed region can be recessed relative to an adjacent surface of the device. This modification can facilitate achieving a blood-replete state in tissue applied to the recessed region. In another example, the recessed region comprises a channel passing through the device so that the tissue can be irradiated through the channel. The provision of a channel in the device allows for an unimpeded light path between a light source used to irradiate the tissue and the irradiated tissue as well as between the tissue and a light collection and/or detection system used in conjunction with the method.

In preferred embodiments, the tissue has an ample supply of blood circulating in capillary beds, such as the fingertip. Other tissues can be used, such as ear lobe, muscle, skin, breast or brain. The subject is preferably a vertebrate, such as a mammal, bird, reptile or fish. Examples of mammals include, but are not limited to, human, bovine, porcine, ovine, murine, equine, canine, and feline. In a most preferred embodiment, the subject is human.

Tissue Modulation Device

The invention disclosed herein provides a device that can be used for modulating blood flow in a tissue. The device is suitable for use in conjunction with methods for measuring an analyte in the tissue. The device can be used noninvasively. The device comprises an upper surface and a lower surface. The upper surface comprises one or more recessed regions adjacent to one or more raised regions. The recessed region can be confluent with the upper surface of the device, or recessed relative to the upper surface. The raised region projects from the upper surface so that application of a portion of tissue to the raised region of the apparatus depresses that tissue relative to a second, adjacent portion of tissue.

In one embodiment, the raised region projects about 50 $\mu$m to about 2 mm from the upper surface of the device. Preferably, the raised region projects about 100 to about 300 $\mu$m from the upper surface. The device can have a single raised region or multiple raised regions, including raised regions of differing heights. Likewise, the device can have a plurality of recessed regions, optionally varying in the extent to which they are recessed relative to the upper surface of the device. The regions can be immediately adjacent to one another, or spaced apart. Preferably, the recessed and/or raised regions are about 20 $\mu$m to about 2 mm apart, and more preferably, about 750 $\mu$m apart.

In preferred embodiments, the device is less than about 8 mm in diameter. More preferably, the diameter of the device is about 4 to about 5 mm. The thickness between the upper surface and the lower surface of at least a portion of the device is preferably less than about 3 mm.

At least one recessed region and/or at least one raised region is optically transparent. The optically transparent region of the device is curved at the lower surface to substantially reduce backscattered light in a light path traveling through the optically transparent region to a light collection system. The device can be optically coupled with a source of electromagnetic radiation and/or with a light detector. In one embodiment, the device includes a light collection system, which can include one or more lenses. In a preferred embodiment, a lens or other light collection system is integrated into one or more raised regions of the device. In another embodiment, the device is part of an apparatus or system that additionally includes means for irradiating the tissue with a light source and/or means for collecting and detecting light emitted by the irradiated tissue. One or more beamsplitters and additional lenses, filters and collimators can be introduced into the light path to modify the light entering and or exiting the tissue.

As illustrated in FIG. 1, a detector 140 can be used in conjunction with the tissue modulation device 110. Multiple detectors can be combined for use with a single tissue modulation device. In one embodiment, a quadrant detector 140 is used, with four sensitive light detectors 160 located on a single small substrate such that it is possible to image light onto each detector individually. Light from a laser 130 is directed to a region of tissue 100 where it penetrates the surface such as the skin. In this embodiment, the remitted light can have a characteristic spectral width and a wavelength other than the incident light wavelength. When this remitted light impinges on a detector 160, an electrical current is produced in proportion to the power delivered by the light.

Each of the four opto-mechanical elements 150 that are optically aligned with the quadrant detector 140 can be employed simultaneously, while each is simultaneously subjected to a chosen amount of tissue modulation. The pattern of tissue modulation that is utilized can define the set of connections made between each of the four detectors 160 in the quadrant detector 140. These connections can be designed so that the amount of signal arriving to the detector from a blood depleted zone is subtracted from the amount of signal which simultaneously emanates from a blood replete zone.

Preferably, the signals are subtracted while in the analog domain, prior to signal digitization or amplification. This affords improved signal to noise and dynamic range compared to that obtainable by amplifiing and digitizing the signals emanating from the blood depleted or blood replete tissue zones prior to signal subtraction. One advantage to subtracting the signals prior to digitization is that each detector is on the same substrate and therefore biased by the same power supply such that the noise associated with environmental fluctuations and the power supply are the same for each detector. The noise is then removed by simple analog subtraction. Because they can be integrated on the same "chip", the detectors and the amplification/subtraction circuitry can be designed and fabricated to share components such as load resistors in amplifiers, so that much of the noise present in the electrical currents produced by these different detectors is correlated. The noise can then be filtered out directly, and amplification of the noise prior to subtraction is avoided. Digitizing and then subtracting noise would lead to an increase in noise in the difference between the signal from a blood replete zone and the signal from a blood depleted zone.

The above quadrant detector embodiment combines in a single element the simultaneous production of spatially distinct regions of tissue modulation with a means to account for fluctuations in the power output of the light source employed. In this embodiment, a single light source can produce four distinct regions which simultaneously experience the same amount of fluctuation in the incident light.

Figure 2:
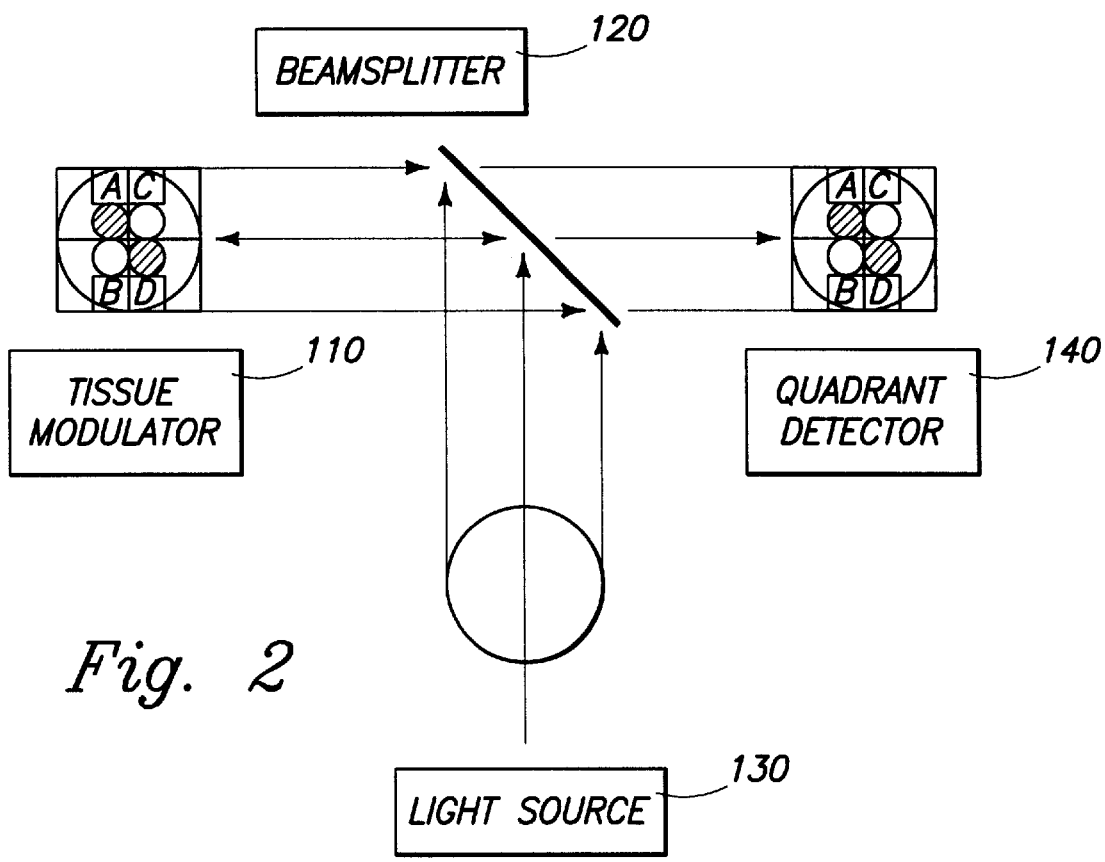
FIG. 2 is further illustrates use of a quadrant detector 140.

FIG. 2 is a representation of a quadrant detector 140 coupled to a tissue modulator 110 and a light source 130. In the diagram, the filled circles and the open circles indicate blood replete and blood depleted regions which are interrogated by an array of parallel rays emanating from the light source 130. The signals emanating from the blood replete regions, represented by A and D, are imaged onto the corresponding quadrants of the detector 140 in a similar fashion as are the signals from the blood depleted regions, represented by B and C. The quadrant detector 140 is wired so that the following processing occurs:

Total quadrant detector output=(A+D)−(B+C)

=(total signal from blood replete regions)−(total signal from blood depleted regions)

=(signal from blood).

The light from the light source 130 hits a beamsplitter 120 such that it is entirely reflected toward the backside of the modulator 110, which is anti-reflection coated. The beamsplitter 120 is shaped so that the residual back-reflection is divergent. This minimizes the amount of the source light which gets directed back through the beamsplitter 120, through a spectrograph/polarizer/notch filter and then to the quadrant detector 140.

The light which traverses the back surface of the modulator is focused by the shape of the front of the modulator 110, into the blood replete and depleted regions as shown in FIG. 2. This light, which traverses the front surface of the modulator, scatters from the tissues in the interaction zone (represented by the intersection of lines in FIG. 2) and some of the scattered light has a trajectory which causes it to re-enter the front surface of the modulator 110. Those rays are re-collimated and sent back toward the beamsplitter 120. Traversing the beamsplitter 120, these rays go through a spectrograph/polarizer/notch filter and then to the quadrant detector 140.

In the embodiment illustrated in FIG. 2, the set of parallel rays illuminates an area spanning the various regions. The blood replete and depleted regions are created by the mechanical contact between the tissue modulator 110 and the finger tip 100 or other portion of the body used in the measurement. The shape of the modulator 110 is designed so that there are four ball lenses which are incorporated into a single monolith. The centers of the balls creating the blood depleted zones (medicated by B and C) are translated outward from the center of the modulator 110 so that they protrude far enough (at least about 200 microns) to push blood out of the points where contact is made with the fingertip 100. At this same position the other two balls (represented by A and D) do not make adequate contact to push blood out of their adjacent tissue.

The approach described above achieves a rejection of background light from the primary light source, a tissue modulated spectroscopic signal, and an automatic analog processing of the signal to minimize noise and increase signal.

Static Tissue Modulation

One strategy for modulating blood flow in a region of living tissue involves application of mechanical pressure or other physical stress that does not fluctuate with time. This strategy is referred to herein as static tissue modulation. During static tissue modulation, the blood content of the interrogated region is kept as constant as possible while measurements are made. One can then take three measurements: one measurement that is indicative of blood volume, one measurement related to the analyte of interest, and one measurement taken at a non-interacting wavelength to assess the quality of the optical connection to the tissue of interest. The quotient of the first two measurements is normalized using the third measurement and is proportional to analyte concentration. The proportionality constant can be determined individually for each user.

Figure 4:
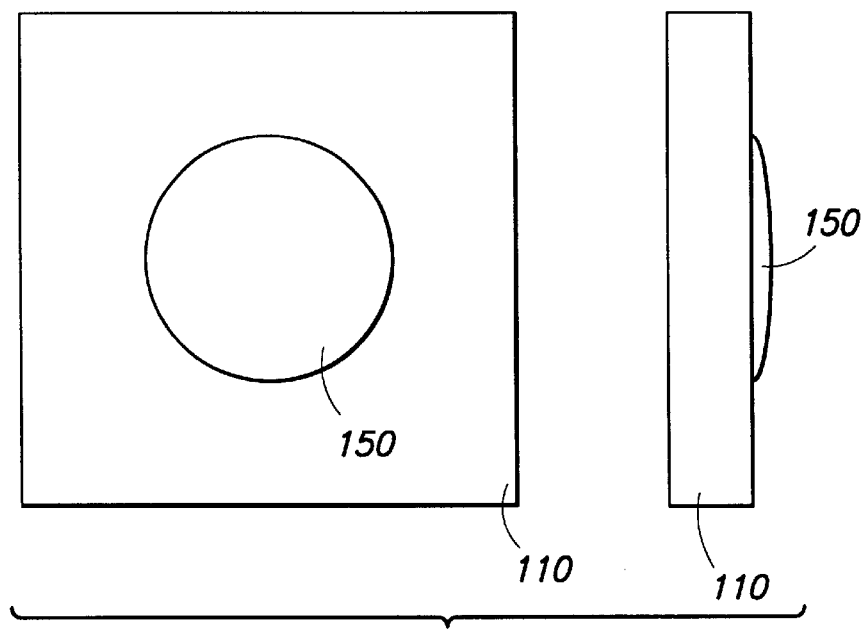
FIG. 4 shows a single plano-convex embodiment of the tissue modulation device 110 in a view from the top and in profile.

In one embodiment designed for static tissue modulation, an optical component is combined with the surface that is used for implementing tissue modulation. In one embodiment, illustrated in FIG. 4, a lens is integrated into a raised region 150 that protrudes from the upper surface of the tissue modulation device 110. In the example illustrated in FIG. 4, a single plano-convex lens is used. Different lenses can be incorporated into the design in accordance with the desired optical and mechanical properties. The examples described herein are based on refractive optics. Those skilled in the art will appreciate that diffractive optics can be incorporated into the device as well.

Pressure is typically applied in tissue modulation, requiring a surface that makes contact with the skin. This surface can be chosen in ways which utilize the surface for advantageous refraction properties and/or spatial encoding of the skin response to spatially encoded pressure. The use of this surface as the primary optical collection surface allows the most efficient light collection because it minimizes the number of optical surfaces as well as the distance between the exposed tissue surface and the first surface of the light collection system.

Figure 3A:
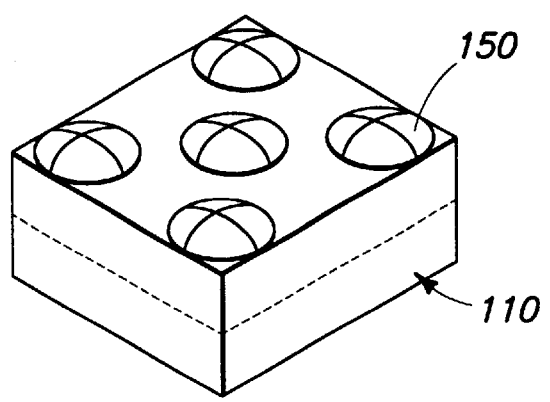
FIG. 3A is a representation of a tissue modulation device 110.
Figure 3B:
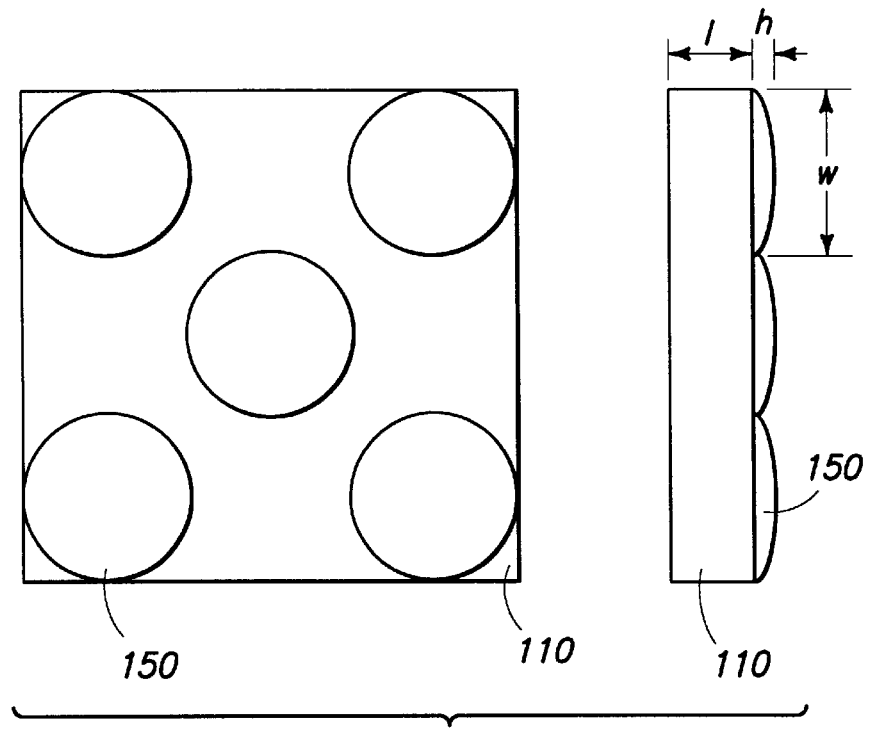
FIG. 3B illustrates top and side views of the device 110 shown in FIG. 3A.

A device having multiple optically transparent regions permits encoding information from spatially distinct regions of tissue. Spatial encoding can provide contrast between one spatial location and another, each receiving different amounts of pressure (tissue modulation) and providing a difference signal indicative of the blood volume per unit area of exposed tissue. FIG. 1 gives one example of a system utilizing the first surface as an optical surface. FIGS. 3A and 3B suggest a few types of patterns which could be useful from a spatial encoding sense. For example, quadrant detectors exist in which four detectors are oriented on an identical but miniature square grid which mimics the orientation of the mini-lenses functioning as tissue modulation sites. In a quadrant detector, the factors contributing to intrinsic detector noise tend to be equal for all the different spatial locations because of their close spatial proximity. Subtractive measurement approaches utilizing the detectors cancels out detector noise.

Figure 5:
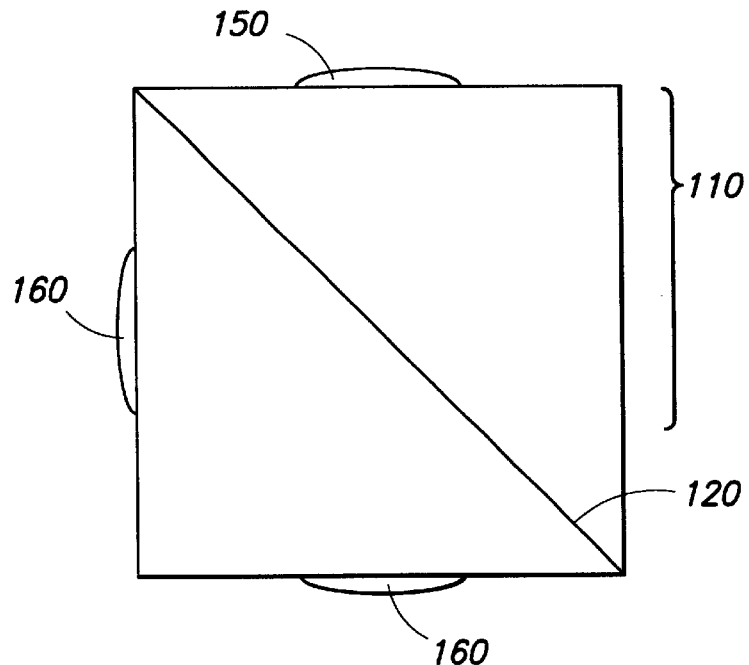
FIG. 5 illustrates a tissue modulation device 110 integrated with a polarizing beamsplitter 120 and extra focusing elements 160. This type of embodiment allows for simultaneous imaging of more than one site and use of a combination of wavelengths.
Figure 6:
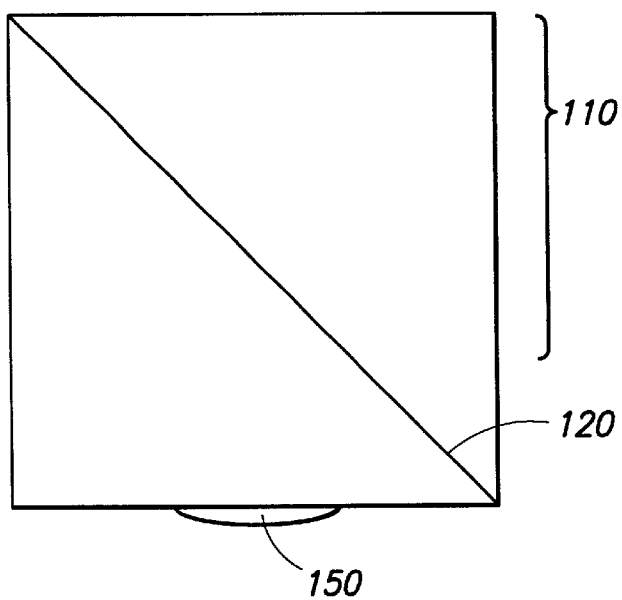
FIG. 6 illustrates a tissue modulation device 110 integrated with a polarizing beamsplitter 120.
Figure 7:
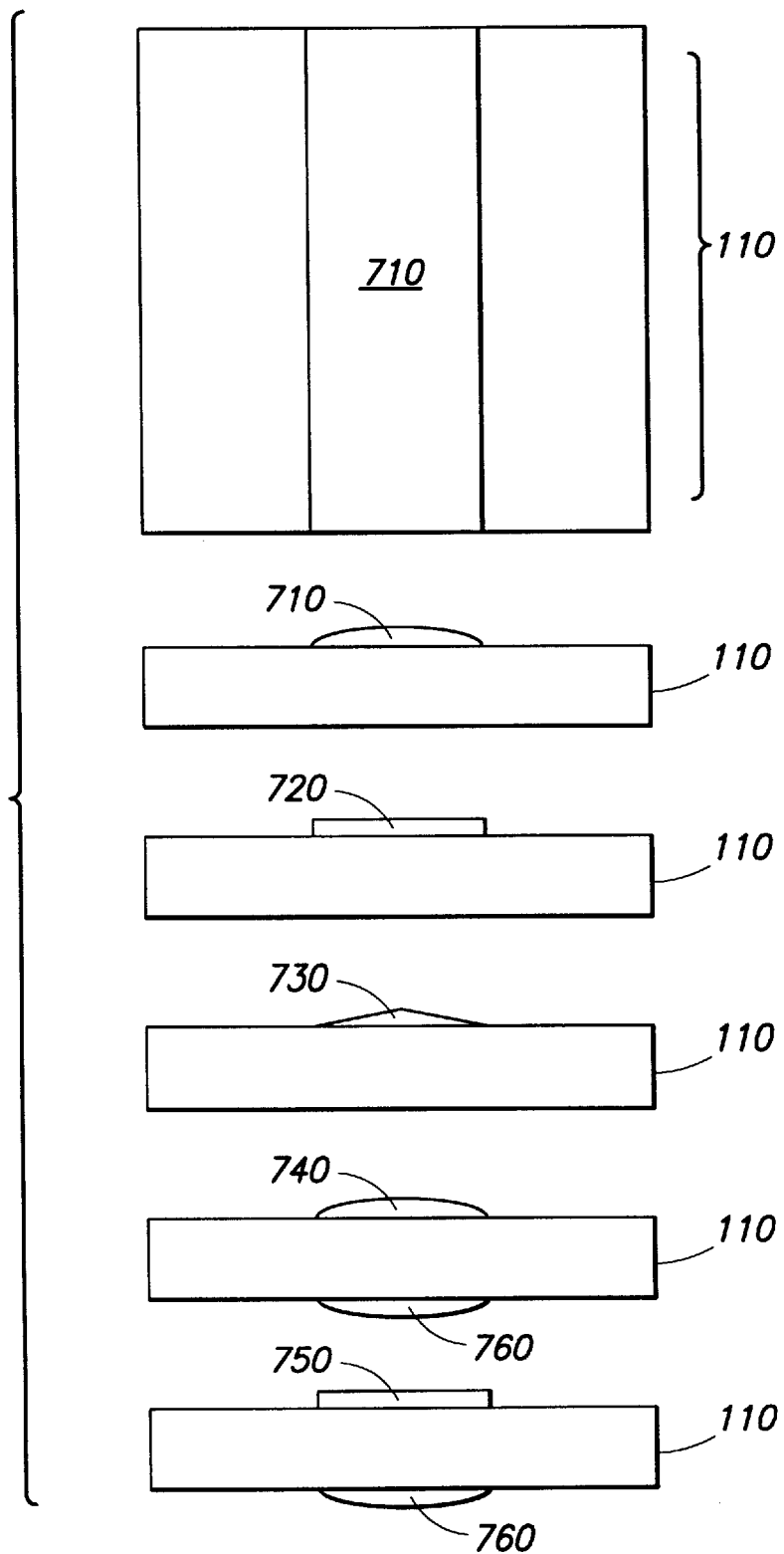
FIG. 7 is a representation of various cylinder lenses 710–750 which may be integrated with the tissue modulation device 110. The first view is a top view illustrating a cylinder lens 710 that runs the length of the device. The remaining views illustrate various types of cylinder lenses 710–750 in cross-section. These examples include a conventional cylinder lens 710, a square cross-section lens with filtering, phase shift/polarization shift 720, a triangular cross-section lens 730, a conventional cylinder lens 740 used in conjunction with an additional focusing element 760, and a square lens cross-section lens with spectral/polarization/phase filter 750 and an additional element 760 for focusing or collimation.

FIGS. 5–7 illustrate various embodiments of the tissue modulation device 110 that can be used to alter the light path. FIGS. 5 and 6 illustrate a device 110 integrated with a polarizing beamsplitter 120 and additional focusing elements 160. These variations can be adapted for use with simultaneous imaging and combinations of wavelengths. FIG. 7 variations on a cylinder lens 710–750 for use with the device 110. In addition, one can incorporate multiple cylinder lenses of varying widths to achieve Hadamard encoding and sophisticated signal processing. Use of confocal techniques allow depth of field rejection of skin surface effects and enhancement of irraditation and collection efficiencies of light passing to and from capillary beds. By varying the height of the raised regions through which light is directed, one can focus light and take measurements from skin using one height and from blood using a second height.

Dynamic Tissue Modulation

In some embodiments, the tissue modulation device is designed so that information can be obtained from a given region of tissue at different points in time. This strategy is referred to herein as dynamic tissue modulation. In dynamic tissue modulation, a given amount of stress and/or pressure is applied to the tissue and then released or reduced. Measurements are made during the time when the equilibrium distribution of blood in the interrogated tissue is reestablished by normal circulation. The components of a concentration measurement, anayte-related signal and blood volume-related signal, are obtained by processing the measurements to correlate the change in signals with the change in blood volume.

One advantage of the dynamic tissue modulation strategy is the amplification of blood-related signals achieved by distinguishing signals that change with blood flow from non-blood-related signals that remain constant as blood flow changes. In addition, temporal or dynamic modulation can be combined with spatial encoding to considerably improve both precision and accuracy of analyte measurements.

The invention provides a device for dynamic tissue modulation. The device comprises means for causing a region of tissue to become blood-depleted, means for releasing the cause of blood-depletion, and means for spectroscopic interrogation of the region of tissue before, during and after depletion of blood in the tissue region. Some embodiments further comprise a means for imposing an optically transparent plate into a position where it can exert sufficient pressure against a skin surface to remove blood from the adjacent capillary bed. Such a plate can comprise both raised and recessed regions to effect spatially selective tissue modulation.

One strategy for causing and subsequently releasing blood-depletion involves use of a continuous sequence of plates that form a circuit or conveyor belt configuration that translates around one or more sprockets. The plate can be rotated into position and the finger or other tissue placed on it so as to achieve a blood-depleted region of tissue. The belt is then quickly translocated sideways, in 0.2 seconds or less for example, by rotating a sprocket. This translocation permits blood to flow back into the previously blood-depleted region. Throughout this process, interrogating light can impinge onto the modulated tissue and spectroscopic measurements can be taken. The amount of pressure applied can be at least about 1 to about 100 g/cm$^2$, and preferably not more than about 1 kg/cm$^2$.

To permit spectroscopic measurement before, during and after tissue modulation, adjacent plates in the conveyor belt can be selected to be opaque or transparent, or to have a gap in the structure. Opaque plates are useful to obtain measurements immediately after pressure is removed, corresponding to the blood-depleted condition. Measurements taken later would be associated with the blood replete condition. With a transparent plate, it is possible to access the tissue of interest before and after the temporal modulation so as to obtain premodulation, steady state blood volume and analyte measurements averaged over a longer period of time. These measurements produce numbers that can be used to calibrate the temporally varying values that are observed during the modulation process. Exclusion of a plate, or provision of a gap between or in the center of a plate, allows spectroscopic interrogation without light interacting with plates. This latter strategy reduces contamination of spectroscopic measurements by unwanted back reflection from a plate.

Thus, in one embodiment, the device comprises a series of alternating recessed and raised regions coupled so as to form a continuous loop, and at least one rotatable sprocket engaged with the loop such that rotation of the sprocket effects rotation of the loop. The recessed regions can be flat, or have a depression in the surface. In one embodiment, the raised region comprises a substantially cylindrical roller. In some embodiments, the recessed region comprises a length having a first end and a second end. The recessed region further comprises a substantially rectangular cross-section and is adjoined at an end by a portion having a substantially circular cross-section.

Figure 8:
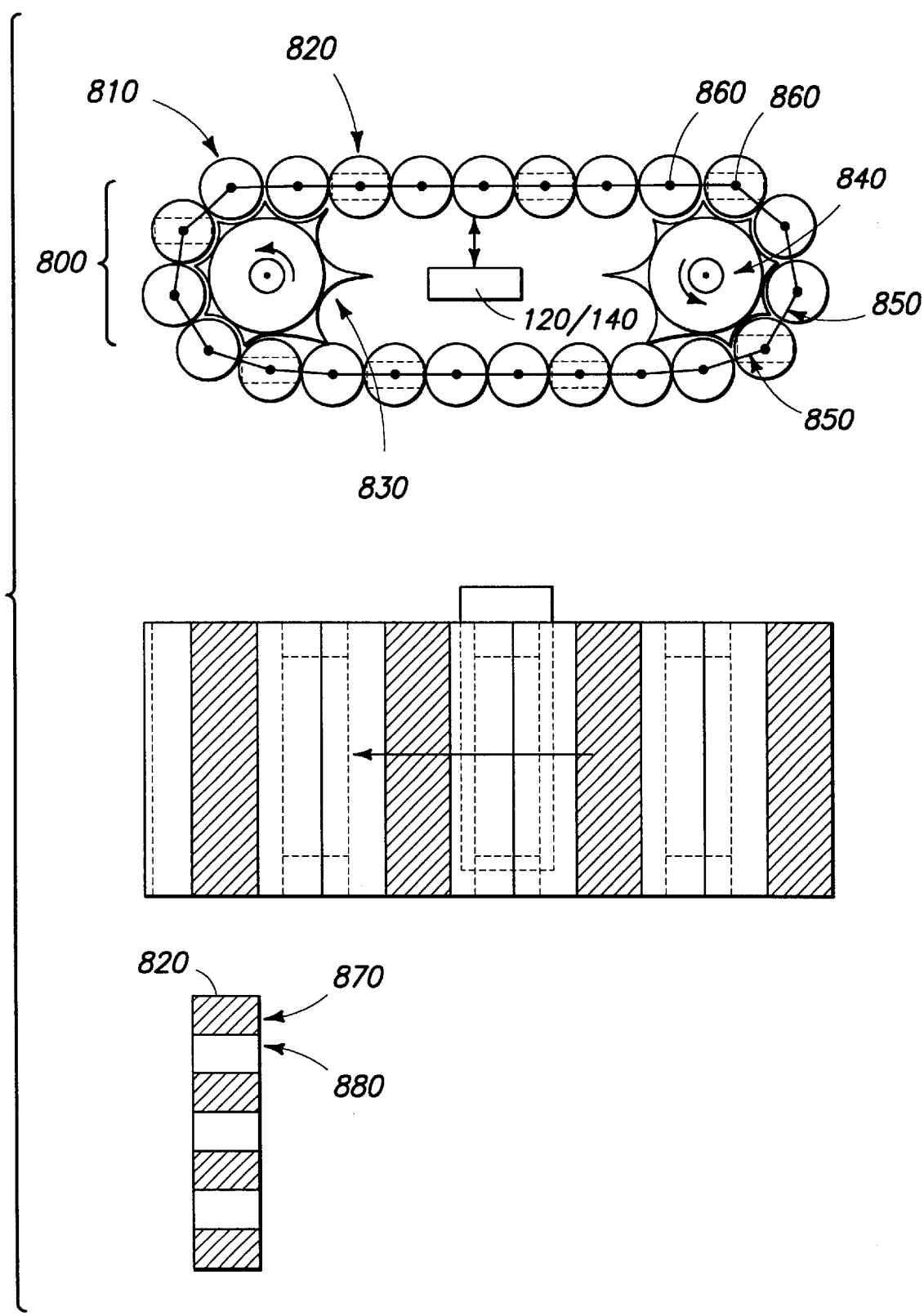
FIG. 8 illustrates a dynamic tissue modulation device 800, including a top view of a series of rollers 810 and slats 820 and a top view of a variation on the slat 820 in which opaque regions 870 alternate with transparent regions 880.
Figure 9:
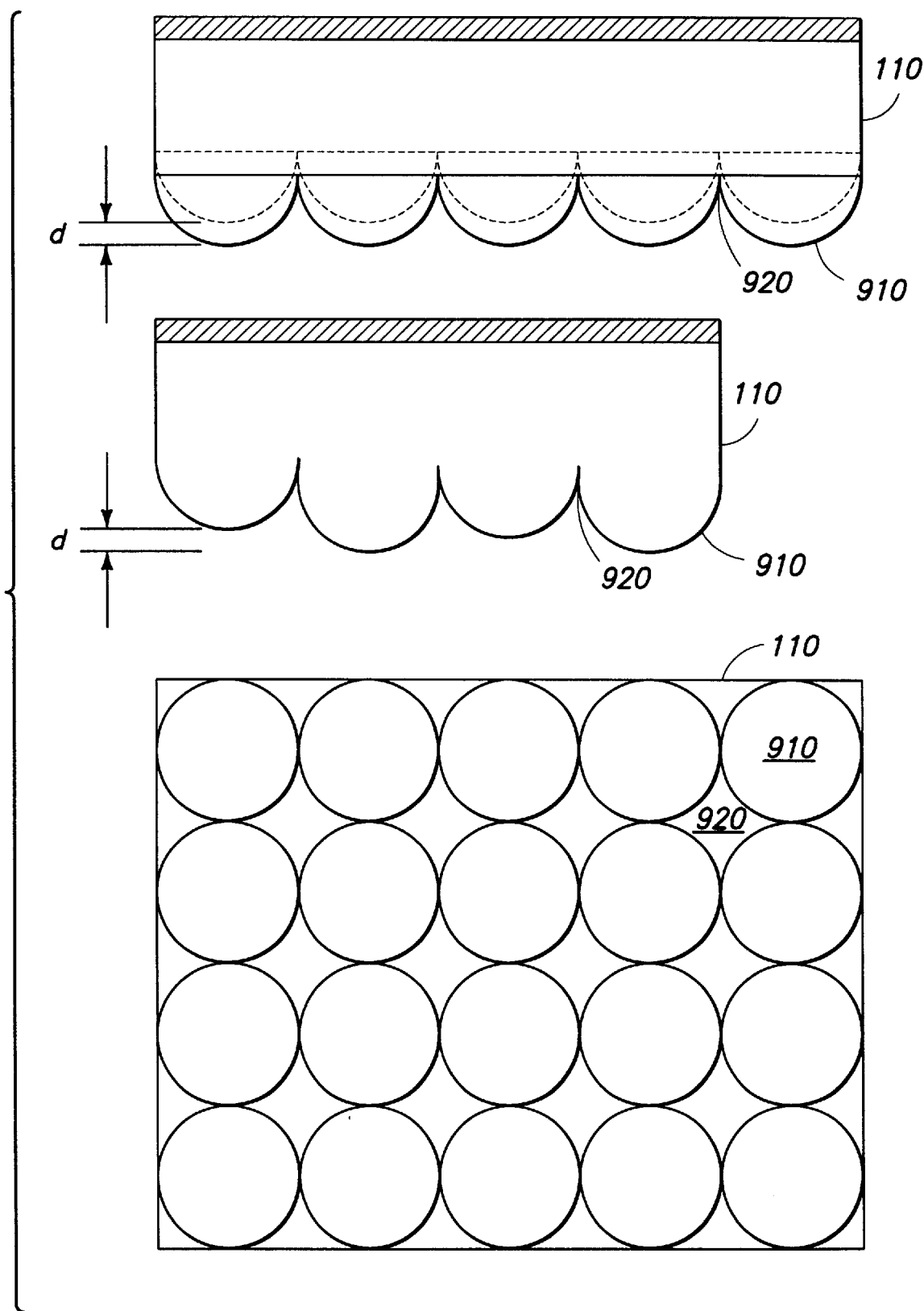
FIG. 9 illustrates side and top views of a tissue modulation device 110 featuring recessed regions 920 and raised regions 910 of varying heights. "d" indicates the height difference between raised regions.

One embodiment is depicted in FIG. 8. A series of rollers 810 and slats 820 are connected by links 850 between their axles 860 or frames 860 (rollers have axles and slats have frames). These rollers 810 and slats 820 constitute a conveyer belt type of arrangement 800. The belt 800 is in turn mounted onto two sprockets 840. The sprockets 840 are turned by a small motor. The device is oriented such that the patient puts his finger (or other body part appropriately positioned relative to the device) onto plates which fix the finger's position and orientation and temperature with respect to the motion of the rollers 810.

The rollers 810 can be nominally opaque and cylindrical with a round cross-section such that they extend outward from their radius sufficiently far that they push on the skin. The slats can be transparent, and as they rotate around to trade positions with the rollers, they do not push on the tissue nearly as much as the rollers. The slats can be of a shape that they function as a cylinder lens in that they have a conventional piano convex or biconvex cross-section. The motion of the rollers is such that they move the blood in and out of the capillaries as they push against the tissue relative to the slats. The motion of the slats is such that they allow efficient exposure of the tissue to light and they allow efficient collection of the light which scatters outward from the tissue. They also allow the light exposure and collection to occur in a precisely defined temporal and spatial proximity to the region which was just squeezed by the preceding roller. The combined action of the slats and rollers is to repetitively squeeze and relax the capillary bed while synchronously probing the tissues with light so as to obtain the blood volume and spectral measurements.

As the rollers move across the finger, the blood is squeezed out into the surrounding regions. When the roller vacates a position, the slat which immediately follows the roller can allow a view of the blood re-entering the previously squeezed region. The slat can be a piece of optically transparent or specially chosen optical filter material that allows light to enter the skin immediately above it and also allows scattered light from within the exposed region to be collected and used for the blood volume and analyte measurement. The slat can also have a shape that is advantageous with regard to the required optical measurements. In one embodiment, the slats are shaped so as to function as cylinder lenses.

In another embodiment, the slats and rollers are shaped so that the pressure on the tissue is not uniform along the entire long axis of the roller. The capillary bed therefore is not uniformly evacuated. In a complementary fashion, the shape of the slat which follows the roller is shaped to expose and collect light into and from both the pressed and nonpressed regions. The collected light is imaged onto a monolithic spatially selective light detector such as a quadrant photodiode or grouping of discrete avalanche photodiodes, so that the non-pressed regions can be automatically subtracted from the pressed regions in the analog domain. This allows a direct background subtraction to be executed while simultaneously obtaining temporal information on the intracapillary blood flow.

The expected signal from a single detector observing scattered blue light would appear as a decreasing function with time, once the slat was in the position formerly occupied by the preceding roller. A decreasing amount of light will reach the detector as time increases. The apparatus has mechanical stops which allow precise and rapid (50–100 msec) exchange of the slats with the rollers. The temporal qualities of this signal are directly correlated with the temporal qualities of the desired blood analyte signals. Thus, phase sensitive or gated detection can be used with the amount of analyte signal modulation being directly traceable to the blood volume modulation. This will also effectively decrease the dynamic range of the signal, allowing an increase in the gain of the detection system (such as, but not limited to, an avalanche photodiode).

In another embodiment, the analyzing employs a fixed combination of opaque rollers and transparent slats. In this embodiment, the apparatus is essentially the same as described above except that the transparent and opaque regions are mechanically fixed in place. No conveyor belt is employed. The person presses his thumb or finger or other tissue region onto the combination, and then pulls it back or pushes it forward while maintaining the pressure of the tissue against the mechanically fixed tissue modulation device. In this embodiment, the transparent regions allow probing of the regions that have just come from the opaque rollers. The timing of this modulation is determined by how quickly the patient pulls or pushes his finger across the apparatus and the amplitude of the modulation is determined by how hard the person is pressing the finger down onto the apparatus.

In another embodiment, transparent rollers and transparent slats are employed. Signal normalzation for this embodiment can employ additional correction.

Those skilled in the art will appreciate various modifications that can be made to the specific embodiments described and that are within the scope of the invention.

What is claimed is:

1. A tissue modulation device comprising an upper surface and a lower surface, wherein the upper surface comprises a recessed region adjacent to a raised region, wherein the device is optically transparent through the upper and lower surfaces in the raised region, wherein the device further comprises an opaque raised region, and wherein the optically transparent region of the device is curved at the lower surface.

2. The device of claim 1, wherein the recessed region is optically transparent.

3. The device of claim 1, wherein the recessed region is recessed relative to an adjacent portion of the upper surface of the device.

4. The device of claim 1, wherein the optically transparent region further comprises an optical filter.

5. The device of claim 1, wherein the optically transparent region comprises a light collection system.

6. The device of claim 5, wherein the light collection system comprises a lens.

7. The device of claim 6, further comprising a laser light source optically coupled with the lens, wherein the lens is capable of focusing light emitted by the laser onto the tissue.

8. The device of claim 6, further comprising a detector optically coupled with the lens, wherein the lens is capable of focusing light emitted by the tissue onto the detector.

9. The device of claim 5, wherein the light collection system comprises a fiber optic collector.

10. The device of claim 1, wherein the substantial curved surface is convex.

11. The device of claim 1, wherein the substantially curved surface is concave.

12. The device of claim 1, wherein the substantially curved surface has a radius of curvature less than about 2 cm.

13. The device of claim 1, wherein the substantially curved surface has a radius of curvature of about 7 mm.

14. The device of claim 2, wherein the upper surface comprises a plurality of raised regions.

15. The device of claim 14, wherein the plurality of raised regions comprises a plurality of lenses.

16. The device of claim 15, wherein the lenses are of differing indices of refraction.

17. The device of claim 14, wherein the raised regions are of differing heights.

18. The device of claim 17, wherein, upon application of external tissue of a subject to the device, at least a first raised region focuses light onto a portion of the tissue comprising blood and at least a second raised region focuses light onto a portion of the tissue comprising skin.

19. The device of claim 14, wherein the edges of the raised regions are about 20 to about 200 microns apart.

20. The device of claim 14, wherein the upper surface further comprises a plurality of recessed regions.

21. The device of claim 1, wherein the raised region is about 50 $\mu$m to about 2 mm in height.

22. The device of claim 2, wherein the upper surface has a diameter of less than about 8 mm.

23. The device of claim 22, wherein the diameter is about 4 to about 5 mm.

24. The device of claim 1 having at least a portion that is less than about 3 mm in thickness between the upper surface and the lower surface.

25. The device of claim 1 optically coupled with a source of electromagnetic radiation and with a light detector.

26. The device of claim 2 further comprising a series of recessed plates and raised plates, wherein the recessed plates have an upper surface comprising at least one recessed region and the raised plates have an upper surface comprising at least one raised region, and wherein the recessed and raised plates are coupled with one another so as to form a continuous loop, and further comprising at least one rotatable sprocket engaged with the loop such that rotation of the sprocket effects rotation of the loop.

27. The device of claim 26, wherein the raised region comprises a substantially cylindrical roller.

28. The device of claim 26, wherein the recessed region comprises a length having a first end and a second end, and wherein the recessed region further comprises a substantially rectangular cross-section and is adjoined at an end by a portion having a substantially circular cross-section.

29. A method of noninvasive spectroscopic measurement of an analyte in a subject comprising:

(a) applying tissue of the subject to a tissue modulation device comprising a recessed region adjacent to a raised region so that the raised region depresses a first portion of tissue relative to a second portion of tissue in apposition to the recessed region, whereby a blood-depleted state is achieved in the first portion of tissue and a blood-replete state is achieved in the second portion of tissue;

(b) irradiating the tissue in a blood-depleted state with electromagnetic radiation having an excitation wavelength;

(c) collecting Raman spectra emitted by the tissue in the blood-depleted state;

(d) irradiating the tissue in a blood-replete state with electromagnetic radiation having an excitation wavelength;

(e) collecting Raman spectra emitted by the tissue in the blood-replete state; and (f) analyzing the collected Raman to determine a concentration of analyte present in the tissue, wherein the analyzing comprises determining the difference between Raman spectra collected in the blood-replete and blood-depleted states.

30. The method of claim 29, wherein the tissue is applied to the device with sufficient pressure to achieve the blood-depleted state in the first portion of the tissue.

31. The method of claim 29, wherein the tissue is applied to the device with sufficient pressure to achieve the blood-replete state in the second portion of the tissue.

32. The method of claim 29, wherein the blood-replete state and the blood-depleted state are achieved in the first portion of the tissue by varying the amount of pressure with which the tissue is applied to the device.

33. The method of claim 29, wherein the blood-replete state and the blood-depleted state are achieved in the first portion of the tissue by alternately applying the raised region and the recessed region to the first portion of the tissue.

34. The method of claim 29, further comprising withdrawing the tissue of the subject from the device so that as to achieve a blood-replete state in the first portion of tissue prior to step (d).

35. The method of claim 29, wherein the irradiating comprises directing light through a channel passing through the device.

36. A tissue modulation device comprising an upper surface and a lower surface, wherein the upper surface comprises a recessed region adjacent to a raised region, wherein the device is optically transparent through the upper and lower surfaces in the raised region, and wherein the optically transparent region of the device is curved at the lower surface, and the optically transparent region further comprises an optical filter.

37. A tissue modulation device comprising an upper surface and a lower surface, wherein the upper surface comprises a recessed region adjacent to a raised region, wherein the device is optically transparent through the upper and lower surfaces in the raised region, wherein the optically transparent region of the device is curved at the lower surface, and the optically transparent region comprises a lens, and wherein the device further comprises a laser light source optically coupled with the lens, wherein the lens is capable of focusing light emitted by the laser onto the tissue.

38. A tissue modulation device comprising an upper surface and a lower surface, wherein the upper surface comprises a recessed region adjacent to a raised region, wherein the device is optically transparent through the upper and lower surfaces in the raised region, wherein the optically transparent region of the device is curved at the lower surface, and the optically transparent region comprises a lens, and wherein the device further comprises a laser light source optically coupled with the lens, wherein the upper surface comprises a plurality of raised regions of differing heights.

39. A tissue modulation device comprising an upper surface and a lower surface, wherein the upper surface comprises a recessed region adjacent to a raised region, wherein the device is optically transparent through the upper and lower surfaces in the raised region, wherein the optically transparent region of the device is curved at the lower surface, and wherein the device is optically coupled with a source of electromagnetic radiation and with a light detector.

40. A tissue modulation device comprising an upper surface and a lower surface, wherein the upper surface comprises a recessed region adjacent to a raised region, wherein the device is optically transparent through the upper and lower surfaces in the raised region, wherein the optically transparent region of the device is curved at the lower surface, wherein the device further comprises a series of recessed plates and raised plates, wherein the recessed plates have an upper surface comprising at least one recessed region and the raised plates have an upper surface comprising at least one raised region, and wherein the recessed and raised plates are coupled with one another so as to form a continuous loop, and further comprising at least one rotatable sprocket engaged with the loop such that rotation of the sprocket effects rotation of the loop.

41. The device of claim 40, wherein the raised region comprises a substantially cylindrical roller.

42. The device of claim 40, wherein the recessed region comprises a length having a first end and a second end, and wherein the recessed region further comprises a substantially rectangular cross-section and is adjoined at an end by a portion having a substantially circular cross-section.

* * * * *

UNITED STATES PATENT AND TRADEMARK OFFICE
CERTIFICATE OF CORRECTION

PATENT NO. : 6,223,063 B1
DATED : April 24, 2001
INVENTOR(S) : Joseph Chaiken and Charles M. Peterson It is certified that error appears in the above-identified patent and that said Letters Patent is hereby corrected as shown below:

<u>Title page,</u>
Item [56], References Cited, U.S. PATENT DOCUMENTS, please add the following references:

| | | | |
|---|---|---|---|
| -- | 4,169,676 | 10/02/79 | Kaiser |
| | 4,655,225 | 04/07/87 | Dähne |
| | 4,975,581 | 12/04/90 | Robinson et al. |
| | 5,086,229 | 02/04/92 | Rosenthal et al. |
| | 5,243,983 | 09/14/93 | Tarr et al. |
| | 5,370,114 | 12/06/94 | Wong et al. |
| | 5,372,135 | 12/13/94 | Mendelson et al. |
| | 5,551,422 | 09/03/96 | Simonsen et al. |
| | 5,553,616 | 09/10/96 | Ham et al. |
| | 5,553,617 | 09/10/96 | Barkenhagen |
| | 5,601,079 | 02/11/97 | Wong et al. |
| | 5,615,673 | 04/01/97 | Berger et al. -- |

FOREIGN PATENT DOCUMENTS, please add:

| | | | |
|---|---|---|---|
| -- | WO 88/06726 | 09/07/88 | PCT |
| | WO 92/15008 | 09/03/92 | PCT |
| | WO 97/13448 | 04/17/97 | PCT |
| | 0 776 628 A2 | 06/24/97 | Europe -- |

OTHER DOCUMENTS, please insert:
-- Anderson, R.R. et al., "The Optics of Human Skin,' The Journal of Investigative Dermatology, Vol. 77, No. 1, 1981, pp. 13-19.

Berger, A.J. et al., "Rapid, Noninvasive Concentration Measurements of Aqueous Biological Analytes by Near-Infrared Raman Spectroscopy," Applied Optics, Vol. 35, No. 1, January 1, 1996, pp. 209-212.

Bhandare, P. et al., "Multivariate Determination of Glucose in Whole Blood Using Partial Least-Squares And Artificial Neural Networks Based on Mid-Infrared Spectroscopy," Applied Spectroscopy, Vol. 47, No. 8, 1993, pp. 1214-1221.

Dou, X. et al., "Biological Applications of Anti-Stokes Ramon Spectroscopy: Quantitative Analysis of Glucose in Plasma and Serum by a Highly Sensitive Multichannel Raman Spectrometer," Applied Spectroscopy, Vol. 50, No. 10, 1996, pp. 1301-1306.

Robinson, M.R. et al., "Noninvasive Glucose Monitoring in Diabetic Patients: A Preliminary Evaluation," Clinical Chemistry, Vol. 38, No. 9, 1992, pp. 1616-1622. --

UNITED STATES PATENT AND TRADEMARK OFFICE
CERTIFICATE OF CORRECTION

PATENT NO.    : 6,223,063 B1
DATED         : April 24, 2001
INVENTOR(S)   : Joseph Chaiken and Charles M. Peterson It is certified that error appears in the above-identified patent and that said Letters Patent is hereby corrected as shown below:

Column 1,
Line 55, "summarued" should read -- summarized --.

Column 8,
Line 57, "anayte-related" should read -- analyte-related --.

Column 11,
Line 46, "substantial" should read -- substantially --;
Line 55, "2" should read -- 1 --.

Column 12,
Line 7, "2" should read -- 1 --;
Line 26, "2" should read -- 1 --.

Signed and Sealed this

Seventeenth Day of December, 2002

JAMES E. ROGAN
*Director of the United States Patent and Trademark Office*